United States Patent [19]

Katzev

[11] Patent Number: 5,002,760

[45] Date of Patent: Mar. 26, 1991

[54] RETINOL SKIN CARE COMPOSITION

[76] Inventor: Phillip K. Katzev, 891 Jamestown Rd., East Windsor, N.J. 08520

[21] Appl. No.: 415,709

[22] Filed: Oct. 2, 1989

[51] Int. Cl.$^5$ .......................... A61K 7/42; A61K 7/44; A61K 7/48; A61K 9/10

[52] U.S. Cl. .......................................... 424/59; 424/60; 514/844; 514/847; 514/938; 514/943; 514/944; 514/969

[58] Field of Search ...................... 514/847; 424/59, 60

[56] References Cited

U.S. PATENT DOCUMENTS

| | | | |
|---|---|---|---|
| 4,608,392 | 8/1986 | Jacquet et al. | 514/725 |
| 4,737,360 | 4/1988 | Allen et al. | 424/195.1 |
| 4,743,442 | 5/1988 | Raaf et al. | 514/725 |
| 4,826,828 | 5/1989 | Wilmott et al. | 514/725 |
| 4,857,321 | 8/1989 | Thomas | 424/195.1 |
| 4,911,919 | 3/1990 | Patel et al. | 424/59 |

OTHER PUBLICATIONS

Cosmetics & Toiletries, 3/76, vol. 91, pp. 87, 89 and 90 to 94, Kass.

*Primary Examiner*—D. R. Ore
*Attorney, Agent, or Firm*—Sachs & Sachs

[57] ABSTRACT

A skin care composition to prevent premature photoaging of the skin of the user includes in addition to basic ingredients, in combination, retinol, a UV absorber and a moisturizer.

12 Claims, No Drawings

RETINOL SKIN CARE COMPOSITION

BACKGROUND OF THE INVENTION

1. Field of the Invention

This invention relates to topical formulations containing retinol, such compositions being of value in the care of the skin and being especially formulated for maximum effectiveness.

2. Description of the Relevant Art

The following U.S. patents relate to skin care compositions, U.S. Pat. No. 4,087,555; 4,268,502; 4,297,374; 4,368,189; 4,372,944; 4,474,763; 4,721,705; 4,722,843; 4,737,360; 4,740,367; 4,743,442; 4,749,563; and 4,760,096. None of these patents, however, disclose or suggest a retinol skin care composition formulated for maximum effectiveness of use for skin care application.

SUMMARY OF THE INVENTION

A skin care composition is provided herein to prevent premature photoaging of the skin of the user, which includes, in addition to basic ingredients, in combination, retinol, a UV absorber and a moisturizer.

The skin care composition herein is formulated and prepared in a preferred manner to enhance the effectiveness of the composition.

DETAILED DESCRIPTION OF THE INVENTION

In accordance with the present invention, there is provided herein a skin care composition which includes, in combination retinol, a UV absorber and a moisturizer. The action of each of these constituents of the skin care composition, in concert is as follows:

Retinol

The Vitamin A derivative retinol work on the genome of the cell to increase production of fibroblasts in the dermal layer of the skin. The fibroblasts increase the production of collagen, elastin, mucopolysaccharides and other connective tissue which improves the strength and resiliency of the skin. These effects enhance the photoprotective property of retinol to prevent and reverse the damage to the skin caused by chronic exposure to sunlight.

UV Absorber

However, use of retinol also causes a thinning of the skin facilitating penetration of ultraviolet rays from the sun. This effect increases the risk of UV exposure which may lead to acute sunburn damage. The use of a UV absorber herein, such as octyl methoxy cinnamate in combination with retinol, is particularly desirable in counteracting the thinning effect.

Moisturizer

The use of retinol for reversing photoaging of skin also causes an increase in transmembrane water loss from the stratum corneum layer Such increased drying of the skin is prevented in the skin formulation of the invention by use of a suitable combination of humectants and protectants. For example, such humectant agents as urea and pyrrolidone carboxylic acid, in combination with steryl, cetyl and polowaxes are effective to restore barrier function to the epidermal layers which may have been adversely affected by retinol action.

In the preferred embodiments of the invention, hydrolyzed collagen also is included in the composition Collagen is a large protein molecule which itself will not penetrate the epidermis of the skin into the dermal layers below. The use of emollients and solvents herein, however, act as a transport vehicle to allow the collagen to be delivered to the dermis. Percutaneous administration of collagen also serves to potentiate the dermal repair properties of retinol to an extent greater than that of retinol alone.

An observed side effect of retinol use is redness and/or direct irritation to the exterior layers of the skin. In this invention, the use of a protectant such a allantoin in combination with the other ingredients in the composition allows the user to maintain skin care treatment with retinol without the risk of erythema or exfoliation often observed with other skin care products.

In summary, the skin composition of the present invention prevents premature photoaging of the skin of the user. In action, the combination of retinol, a UV absorber and moisturizer acts to potentiate the desirable activity of retinol, particularly within the lower dermal layers, while subduing the undesirable side effects of retinol.

Furthermore, the oils and conditioners present in the composition allow better penetration of retinol to the lower layers of of collagen where beneficial action can occur.

The skin care composition of the invention includes the following ingredients as shown in the table.

TABLE

Skin Care Composition of Invention

| Ingredients | Suitable % by Weight | Preferred % by Weight |
|---|---|---|
| Moisturizer (Humectants) | | |
| NaPCA* | 0.5–1.0 | 0.8 |
| NaCl | 0.1–0.5 | 0.3 |
| Glycerin | 0.2–1.0 | 0.6 |
| Urea | 0.1–1.0 | 0.4 |
| | 0.9–3.5 | 2.1 |
| Waxes and Oils | | |
| Steryl wax | 0.5–2.0 | 1.0 |
| Cetyl wax | 0.5–2.0 | 1.0 |
| Apricot oil | 0.02–0.20 | 0.07 |
| Avocado oil | 0.02–0.20 | 0.07 |
| Sesame oil | 0.02–0.20 | 0.07 |
| Olive oil | 0.02–0.20 | 0.07 |
| Coconut oil | 0.2–1.0 | 0.6 |
| | 2.0–5.8 | 2.6 |
| Emulsifiers | | |
| Squalene | 0.1–0.5 | 0.3 |
| Polawax | 0.3–1.5 | 1.0 |
| | 0.4–2.0 | 1.3 |
| Preservatives | | |
| Methyl paraben | 0.05–0.30 | 0.20 |
| Propyl Paraben | 0.05–0.30 | 0.13 |
| | 0.10–0.60 | 0.33 |
| Smootheners/softeners | | |
| Aloe Vera | 0.2–1.2 | 0.7 |
| Allantoin | 0.5–1.5 | 1.2 |
| | 0.7–2.7 | 1.9 |
| Conditioners | | |
| Stearylamidopropyl dimethylamine lactate (SDM) | 1–5 | 3.5 |
| Dimethyldistearyl ammonium chloride (Protoquat 2HT-75% active) | 1–5 | 2.7 |
| | 2–10 | 6.2 |
| Perfumes | | |
| Lavender | 0.05–0.5 | 0.2 |

TABLE-continued
Skin Care Composition of Invention

| Ingredients | Suitable % by Weight | Preferred % by Weight |
| --- | --- | --- |
| UV Absorbers | | |
| Octyl methoxy cinnamate | 2–10 | 5 |
| Fiber Protein | | |
| Hydrolyzed collagen | 0.05–0.20 | 0.15 |
| Vitamins | | |
| Vitamin A, D3, E, Pantothenol | 0.01–0.1 each | 0.04 |
| Retinol | 0.01–0.1 | 0.04 |
| | 0.05–0.5 | 0.08 |
| Solvent | | |
| Water, purified USP | 75–85 | 80 |

The composition of the present invention is prepared in the following manner.

The calculated amount of water is placed in a jacketed tank and the temperature is brought to 140 degrees F. (60 degrees C.), then the appropriate amounts of the following ingredients are added in the order designated; hydrolyzed collagen, methyl paraben, propyl paraben, SDM, 2HT-75, steryl wax, cetyl wax, polawax, glycerin, coconut oil, allantoin, urea, squalene, apricot oil, avocado oil, sesame oil, olive oil and octyl methoxy cinnamate. The total amount of ingredients added then are allowed to dissolve and/or be dispersed in the heated water medium. Mixing is then commenced to form a uniform suspension. The temperature of the mixture then is reduced to 90 degrees F. (32.2 degrees C.) and the following ingredients are added: Vitamins A, D3, E and pantothenol followed by aloe vera and retinol. Mixing is continued. Then the NaPCA ingredient is added while continuing the mixing process. Then NaCl is dissolved in an aliquot of water and the solution is added slowly with mixing. At this point, the product begins to gel and becomes heavy. The resultant skin composition then is homogenized for commercial use.

The skin care composition of the invention is characterized by being soap free, non-oily, petroleum and mineral oil-free, and containing no lanolin or para-aminobenzioc acid.

A preferred skin care composition of the invention comprises:

| Ingredient | Percent |
| --- | --- |
| Purified water | 79.68 |
| Hydrolyzed collagen | 0.149 |
| Methyl paraben | 0.1865 |
| Propyl paraben | 0.13 |
| SDM-Stearylamidoprophyl dimethylamine lactate | 3.576 |
| 2HT-75-Dimethyldistearyl ammonium chloride | 2.686 |
| Steryl wax | 0.93 |
| Cetyl wax | 0.93 |
| Polawax | 0.93 |
| Glycerin | 0.6215 |
| Coconut oil | 0.6215 |
| Allantoin | 1.258 |
| Urea | 0.42 |
| Squalene | 0.298 |
| Apricot oil | 0.075 |
| Avocado oil | 0.075 |
| Olive oil | 0.075 |
| Sesame oil | 0.075 |
| Octyl methoxy cinnamate | 5.0 |
| Vitamin A | 0.037 |

-continued

| Ingredient | Percent |
| --- | --- |
| Vitamin D3 | 0.037 |
| Pantothenol | 0.037 |
| Aloe vera | 0.746 |
| Lavender | 0.234 |
| Retinol | 0.039 |
| NaPCA-pyrolidone carboxylic acid | 0.789 |
| NaCl | 0.326 |

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A skin care composition which consists essentially of about 0.01 to 0.1% by weight retinol, 2 to 20% by weight UV absorber, 0.9 to 3.5% by weight humectant, about 2.0 to 5.8% by weight waxes and oils, about 0.4 to 2.0% by weight emulsifiers, about 0.10 to 0.60% by weight preservatives, about 0.7 to 2.7% by weight smootheners/softeners, about 2 to 10% by weight conditioners, about 0.05 to 0.5% by weight perfumes, about 0.05 to 0.20% by weight hydrolyzed collagen, about 0.04 to 0.4% by weight vitamins other than retinol selected from the group consisting of vitamin A, vitamin D, vitamin E and pantophenol, and about 75 to 85% by weight water.

2. A skin care composition according to claim 1 in which the UV absorber is octyl methyl cinnamate.

3. A skin care composition according to claim 1, which contains about 0.04% by weight retinol, about 5% by weight octyl methyl cinnamate and about 2.1% by weight moisturizer.

4. A skin care composition according to claim 1 in the form of a skin cream, face cream, lotion, ointment or gel.

5. A skin composition according to claim 1, wherein the conditioners include stearylamidopropyl dimethylamine lactate and dimethyldistearyl ammonium chloride.

6. A skin care composition according to claim 1 which perfumes include lavender.

7. A skin care composition according to claim 1 which smoothener includes aloe vera and allantoin.

8. A skin care composition according to claim 1 wherein the humectants include pyrrolidone carboxylic acid, sodium salt sodium chloride, glycerin and urea.

9. A skin care composition according to claim 1 wherein the waxes and oils include steryl and cetyl wax, and apricot, avocado sesame, olive and coconut oils 10. A skin composition according to claim 1 wherein the emulsifiers include squalene.

11. A skin care composition according to claim 1 wherein said preservatives include methyl and propyl paraben 12. A skin care composition comprising:

| Ingredient | Percent |
| --- | --- |
| Purified water | 79.68 |
| Hydrolyzed collagen | 0.149 |
| Methyl paraben | 0.1865 |
| Propyl paraben | 0.13 |
| SDM-Stearylamidopropyl dimethylamine lactate | 3.576 |

-continued

| Ingredient | Percent |
| --- | --- |
| 2HT-75-Dimethyldistearyl ammonium chloride | 2.686 |
| Steryl wax | 0.93 |
| Cetyl wax | 0.93 |
| emulsifier wax | 0.93 |
| Glycerin | 0.6215 |
| Coconut oil | 0.6215 |
| Allantoin | 1.258 |
| Urea | 0.42 |
| Squalene | 0.298 |
| Apricot oil | 0.075 |

-continued

| Ingredient | Percent |
| --- | --- |
| Avocado oil | 0.075 |
| Olive oil | 0.075 |
| Sesame oil | 0.075 |
| Octyl methoxy cinnamate | 5.0 |
| Vitamin A | 0.037 |
| Vitamin $D_3$ | 0.037 |
| Pantothenol | 0.037 |
| Aloe vera | 0.746 |
| Lavender | 0.234 |
| Retinol | 0.039 |
| NaPCA-pyrolidone carboxylic acid | 0.789 |
| NaCl | 0.326 |

\* \* \* \* \*